United States Patent [19]

Redepenning

[11] Patent Number: 5,413,693
[45] Date of Patent: * May 9, 1995

[54] ELECTROCRYSTALLIZATION OF STRONGLY ADHERENT BRUSHITE COATINGS ON PROSTHETIC ALLOYS

[76] Inventor: Jody G. Redepenning, 920 Manchester Dr., Lincoln, Nebr. 68528

[ * ] Notice: The portion of the term of this patent subsequent to May 10, 2011 has been disclaimed.

[21] Appl. No.: 176,829

[22] Filed: Jan. 3, 1994

Related U.S. Application Data

[63] Continuation of Ser. No. 638,104, Jan. 4, 1991, Pat. No. 5,310,464.

[51] Int. Cl.⁶ ............................................. C25D 11/36
[52] U.S. Cl. ..................................... 205/318; 623/16; 623/901
[58] Field of Search ........................ 204/180.2, 181.3; 205/318; 623/16, 901

[56] References Cited

U.S. PATENT DOCUMENTS

| | | | |
|---|---|---|---|
| 4,366,183 | 12/1982 | Ghommidh et al. | 427/2 |
| 4,490,219 | 12/1984 | Bindra et al. | 204/23 |
| 4,522,892 | 6/1985 | Shindow | 428/628 |
| 4,806,218 | 2/1989 | Hemminger | 204/180.2 |
| 4,808,281 | 2/1989 | Tison | 204/56.1 |
| 5,129,905 | 7/1992 | Constantz | 606/76 |
| 5,205,921 | 4/1993 | Shirkanzadeh | 205/318 |

FOREIGN PATENT DOCUMENTS

| | | |
|---|---|---|
| 0264353 | 10/1987 | European Pat. Off. . |
| 0264354 | 10/1987 | European Pat. Off. . |

*Primary Examiner*—John Niebling
*Assistant Examiner*—Arun S. Phasge
*Attorney, Agent, or Firm*—Schmeiser, Morelle & Watts

[57] ABSTRACT

An electrolytic method for providing bone-emulating, phosphate coatings on prosthetic appliances. Such coatings serve to enhance bone fixation after implantation of the appliances. The method of the invention is an electrolysis process wherein the appliance to be coated is immersed in a phosphate-containing electrolyte to serve as the cathode of the electrolysis process. When current is applied to the electrolysis cell, the electrolyte solution, which includes calcium ions and dihydrogen phosphate ions, is caused to rapidly increase in (localized) pH proximate the cathode element. The localized pH increase creates a supersaturated local condition causing less soluble calcium phosphate salts to crystallize out of the electrolyte solution and adhere to the cathode, thus effecting thereon a coating of brushite.

5 Claims, 3 Drawing Sheets

ELECTROCRYSTALLIZATION OF STRONGLY ADHERENT BRUSHITE COATINGS ON PROSTHETIC ALLOYS

This application is a continuation of application Ser. No. 07/638,104, filed on Jan. 4, 1991, now U.S. Pat. No. 5,310,464.

BACKGROUND OF THE INVENTION

1. Field of the Invention

This invention relates generally to a procedure for coating prosthetic alloys with a bone-emulating substance and, more particularly, to electro-stimulated phosphate (brushite) growth on metallic conductive substrates.

2. Background Information

Although the mechanism by which fixation of bone to a transplant occurs is somewhat beyond the scope of the instant disclosure, is has been observed that the coating of metallic prostheses with phosphate ceramics has received a great deal of recent attention because of the apparent propensity of these coatings to accelerate bone fixation during the early stages following implantation. Current articles in the literature have given ample reason to believe that the rate of metal ion release from some alloys can be reduced by calcium phosphate coatings. Further, reviews concerning applications of hydroxyapatite coatings on metallic implants were given significant treatment by Ducheyne, P.; Lemons, J. E.; Eds.; "Bioceramics: Material Characteristics Versus In Vivo Behavior", New York, The New York, Academy of Sciences, 1988.

The most frequently used means or process for the deposition of calcium phosphate materials on prosthetic alloys is by way of plasma or flame spraying. There was recently reported by Takayuki Shimamune and Masashi Hosonuma in *Chemical Abstracts*, volume 109:11784d and volume 109:11785e, data on a calcium phosphate-coated medical composite implant material and a process for its manufacture. Therein, it is indicated that a calcium phosphate-coated compatible composite material, comprising a metallic substrate and an oxide layer of more than one metal selected from the group consisting of titanium, zirconium, hafnium, vanadium, niobium, tantalum, tin, cobalt, aluminum, chromium, molybdenum and tungsten is overlayed with a layer of calcium phosphate which can be produced by plasma or flame spraying. This composite has an affinity for the tissue of bone or teeth and finds its use as an implant material for artificial bone, teeth and teeth roots, or as a bonding material for such implant materials.

Also significant, and as disclosed in the *Chemical Abstracts* references are European Patent applications 0,264,353 and 0,264,354, both made by Shimamune and Hosonuma. These disclosures teach a composite material and a process for the production thereof which comprises a metallic substrate having thereon an oxide layer, the oxide layer consisting essentially of the oxide of one or more metals denoted in the previously mentioned group, and thereafter a calcium phosphate overlay on the oxide layer. The composite is made by oxidizing a metallic substrate, either thermally or electrolytically, to form a layer of the oxide or the metallic substrate component alone or a layer of mixed oxide of the metallic substrate component and a metal component in the electrolyte. Alternatively, heating of the metallic substrate is accomplished to stabilize the surface thereof; and, then a coating of calcium phosphate compound is formed on the surface. Essentially, the Shimamune et al methodology comprises two distinct processes. The first, the perhaps preferred embodiment, is a process used to produce a calcium phosphate compound-coated composite material suitable as an implant material. This comprises thermally oxidizing a metallic substrate to form, on the surface of the metallic substrate, a layer of the oxide of the metallic substrate component, such providing excellent corrosion resistance in the living body. Then, there is formed on the oxide coating a layer of calcium phosphate compound such as apatite hydroxide, which has been determined to have affinity to the living body on the surface of the aforementioned oxide layer. The second Shimamune et al. embodiment is a process for producing a calcium phosphate compound-coated composite material, also suitable as an implant, which comprises electrolizing a metallic substrate in an electrolyte to form on the surface thereof a coating of the oxide of the metallic substrate component alone or a mixed oxide of the metallic substrate component and a metal component of the electrolyte. Thereafter, as in the first embodiment, there is formed on the oxide, a calcium phosphate coating such as apatite hydroxide.

When the metallic substrate is made of stainless steel or a cobalt-chromium alloy, unlike the case wherein the metallic substrate is made of titanium or a titanium alloy, it is necessary to become highly selective in the electrolyte usage. Shimamune et al. teach that, if anode polarization is carried out in an acidic solution, the metal surface is dissolved and the desired oxide layer becomes difficult to obtain. Continuing, they teach that, in a strongly alkaline solution, the oxide on the surface of the metallic substrate is partially dissolved and thus, in some cases, a sufficiently grown oxide layer cannot be obtained. The limitation which is therefore placed on the process is that it becomes necessary to choose an electrolyte having a pH of 6 to 13. Quite matter-of-factly, Shimamune et al. insist that the method of forming the calcium phosphate coating and the conditions under which the method is carried out are not critical.

The proposition that an electrolytic method for phosphate deposition on an alloy serving as the anode is not only commonplace, but also the current state-of-the-art, finds substance in the issuance of a patent in 1985 to Shindow et al. (U.S. Pat. No. 4,522,892). Shindow et al. teach a steel strip having phosphate-coating property produced by subjecting at least one surface of a steel strip to electrolytic treatment in which the strip serves as an anode. Its surface is brought into contact with an aqueous solution containing at least one phosphate selected from the group consisting of alkali metal phosphates and ammonium phosphate; the solution having a concentration of phosphoric anions of 0.05 mole/L or more and a pH of from 4 to 7. Thus, the noteworthy factors in the Shindow process are the electrolytic formation of the coating on an anode at a pH between 4 and 7. In contrast to the procedure I have developed, it is particularly noteworthy that the process of Shindow et al. is an oxidation which occurs in an electrolyte solution that does not contain the cation to be deposited. The contention that an electrophoretic method of phosphate deposition on a metal serving as the cathode reflects the current state-of-the-art, finds substance in the issuance of a patent in 1989 to Hemminger et al. (U.S. Pat. No. 4,806,218). Therein, electrophoresis is termed cataphoretic because the final coating is placed on the tungsten element or wires while they act as a cathode. Hemminger et al. avoid a certain degree of erosion of the electrode by first applying polarity and treating it as an anode for the purposes of incipient coating; thereafter, the polarity is reversed and the element to be coated spends the duration of the electrophoretic processing period as a cathode. As in the previous teachings, it is the purpose of these patentees to place an oxide coating on the electrodes and, therefore, the electrolyte is generally devoid of phosphate ions. Hemminger et al. differ from Shindow et al. in that the electrode of interest is a cathode which is used electrophoretically, while Shindow uses the electrode of interest as an anode in an electrolytic cell (as was the case in the procedure of Shimamune et al.).

Electrophoretic deposition of phosphate materials has recently received a good deal of professional attention. It is seen that, in most conventional and state-of-the-art coating processes, particles are suspended in a liquid and, in the presence of a large electric field, are driven onto an electrode. Analysis of these coatings, after sintering, indicates the presence of hydroxyapatite and tricalcium phosphate. These techniques are particularly attractive because irregularly shaped substrates, such as are employed in the various prostheses, can be coated conveniently and relatively inexpensively.

Generally speaking, electrolytic deposition methods should grow to greater popularity since most of the heretofore conventional methods of preparing implants with phosphate coatings have employed flame spraying and plasma spraying. With these latter procedures, heating of the substrate surface can be extensive and thermal decomposition of the material being sprayed is often observed. Other high temperature techniques, such as dip coating and sputter coating, can also suffer from thermal degradation, inconveniences and disabilities which make electrolytic deposition a superior coating procedure.

SUMMARY OF THE INVENTION

I have devised an electrolytic method for preparing phosphate coatings on cathodes which is superior in the way of obtaining that goal but avoids the disabilities and disadvantages of the earlier and conventional art. This new, electrolytic process is especially attractive because highly irregular objects can be coated relatively quickly at low temperatures. Additionally, a high degree of control of deposit crystallinity can be obtained using my procedure and, because the coating is formed on an alloy used as a cathode, a departure from the preceeding art, corrosion of the metal surface is minimized during the deposition process.

All deposits disclosed herein were formed at room temperature from aqueous solutions which contained calcium ions and dihydrogen phosphate ions. Deposits were typically formed while controlling the current throughout the course of the deposition, although deposits can also be obtained by controlled potential electrolysis. Oxygen was not excluded. The process is distinct and is one of electrolysis, not electrophoresis. By applying a negative potential to the object to be coated, hydrogen is evolved and the pH at the surface of the cathode is abrubtly increased. The pH increase converts $H_2PO_4^-$ ions to $HPO_4^{2-}$ ions and results in the crystallization of the less soluble calcium phosphates from the electrolyte onto the cathode. By increasing the current, the pH and the pH gradient near the cathode increase, thus producing more nucleation sites and faster crystal growth. Thus, I teach a form of controlled crystal growth on a cathodic prosthetic alloy or other suitable electrode which is placed into an electrolysis process apparatus. The process may be set up in any simple laboratory by anyone having rudimentary knowledge of the electrolysis technique and the capability of preparing the requisite electrolyte solutions containing calcium ions and dihydrogen phosphate ions.

DETAILED DESCRIPTION OF THE PREFERRED EMBODIMENT

Figure 1A:
FIGS. 1A and 1B are scanning electron micrographs of electrolytically deposited calcium phosphate coatings on 316L stainless steel.

Given the number of arthroplastes performed yearly, the need for a physically stable, biocompatible material which can be easily deposited on implant surfaces is considerable. It has been recently reported, in a prominent medical journal, that an estimated 120,000 total hip implants are required yearly in the United States. As early as 1986, it was estimated that, by 1990, the annual joint prostheses requirements would reach 500,000. Thus, a process for economically coating a metallic prostheses with phosphate ceramic, notably the various calcium phosphate coatings, becomes compelling when viewed in the light of the ability of these coatings to accelerate bone fixation during the early recuperative stages after implantation.

Before detailing the various processes which enabled me to obtain the desired crystalline phosphate coatings, I will clarify the difference between the form of present state-of-the-art electrodeposition and the instant invention. Electrophoresis is the impelling of charged particles (suspended in a liquid medium) towards an anode and/or cathode (electrodes) between which there is established an electric field. At rates depending upon the magnitude of the electric field, the mass of the particles in suspension, and other physical parameters, positively charged particles will be impelled onto the cathode, while negatively charged particles will impact the anode.

Electrolysis, on the other hand, is associated with a change in oxidation state of species at both the cathode and the anode of an electrochemical cell. In many cases, electrolysis is a deleterious process to be avoided if it occurs during an electrophoretic deposition. It is on this distinction that I base my new electrodepositional method, which I define as an electro-stimulated crystalline phosphate growth on metallic conductive substrates. The electro-stimulation is associated, as previously mentioned, with the passage of an electrical current through the working electrode. The crystalline phosphate growth is produced by a redox process not by an impacted aggregation of particles. I deviate from the general case in that my electrode of deposition (the prosthetic or alloy element) is used as the cathode which controls the pH in the vicinity of the substrate throughout the depositional scheme. This procedure permits one to exercise a high degree of control over deposit crystallinity and minimizes (or obviates) corrosion of the metal surface during the depositional activity. Additionally, by controlling the current density, it is possible to control the deposit morphology.

Having set the actual stage for the following experiment, it is only necessary to describe the physical plant that is used to realize the instant invention. A conventional electrolysis apparatus is set up in which the device to receive phosphate deposition is established as the cathode. The electrolyte comprises an aqueous solution containing $Ca^{2+}$ and dihydrogen phosphate ions. No deliberate attempt is made to exclude oxygen and I feel that there is no degradation in the results because of this purposeful non-exclusion. Crystallization occurs, once the electrical current is passed, as a result of an electrolytically induced pH gradient near the cathode surface. Upon reduction of the electrolyte solution, a variety of half reactions can occur. The dominant reaction is a reduction of water to hydrogen gas and hydroxyl ions $(OH)^-$. This reaction results in a localized pH increase in the vicinity of the cathode. The pH increase near the surface of the electrode converts $H_2PO_4^-$ to $HPO_4^-$ and results in the crystallization of less soluble calcium phosphates. By increasing the current, both the pH and the pH gradient near the electrode increase, thus producing more nucleation sites and faster crystal growth. The following experimental regimen indicates results obtained in the laboratory that are totally consistent with the aforementioned rationale.

Experimental

A cathode is prepared by using a device (prosthesis) comprised of 316L stainless steel. To form the deposit depicted in FIG. 1A, the electrolysis is run over a period of 2 hours 13 minutes at 1 $mA/cm^2$ for a total of 8 $C/cm^2$. In FIG. 1B, a calcium phosphate deposit at 10 $mA/cm^2$ resulted from a total of 5 $C/cm^2$ being passed over 8 minutes 20 seconds. Larger crystals are produced, as expected, at the lower current density. Additional to nucleation arguments, the vigorous rate of hydrogen evolution observed at 10 $mA/cm^2$ is partially responsible for the decreased crystal size in this case.

Figure 1B:
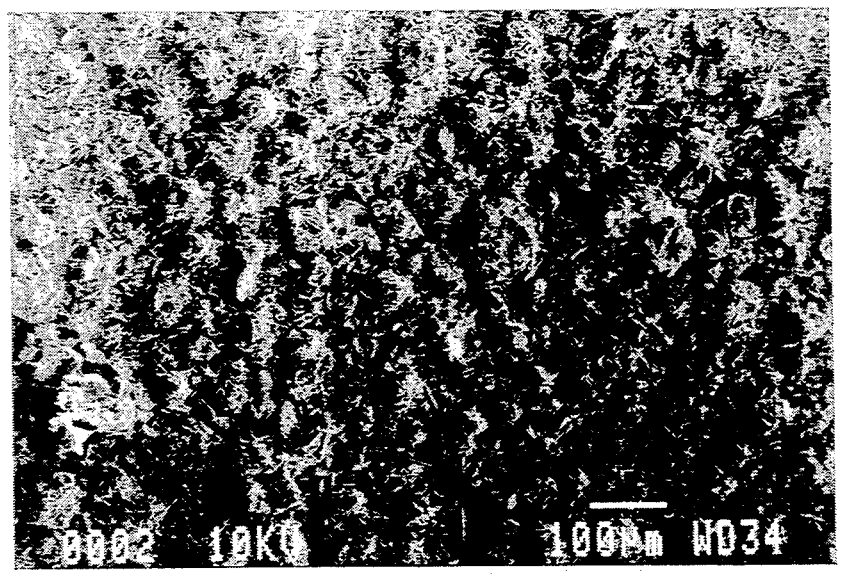
Figure 2:
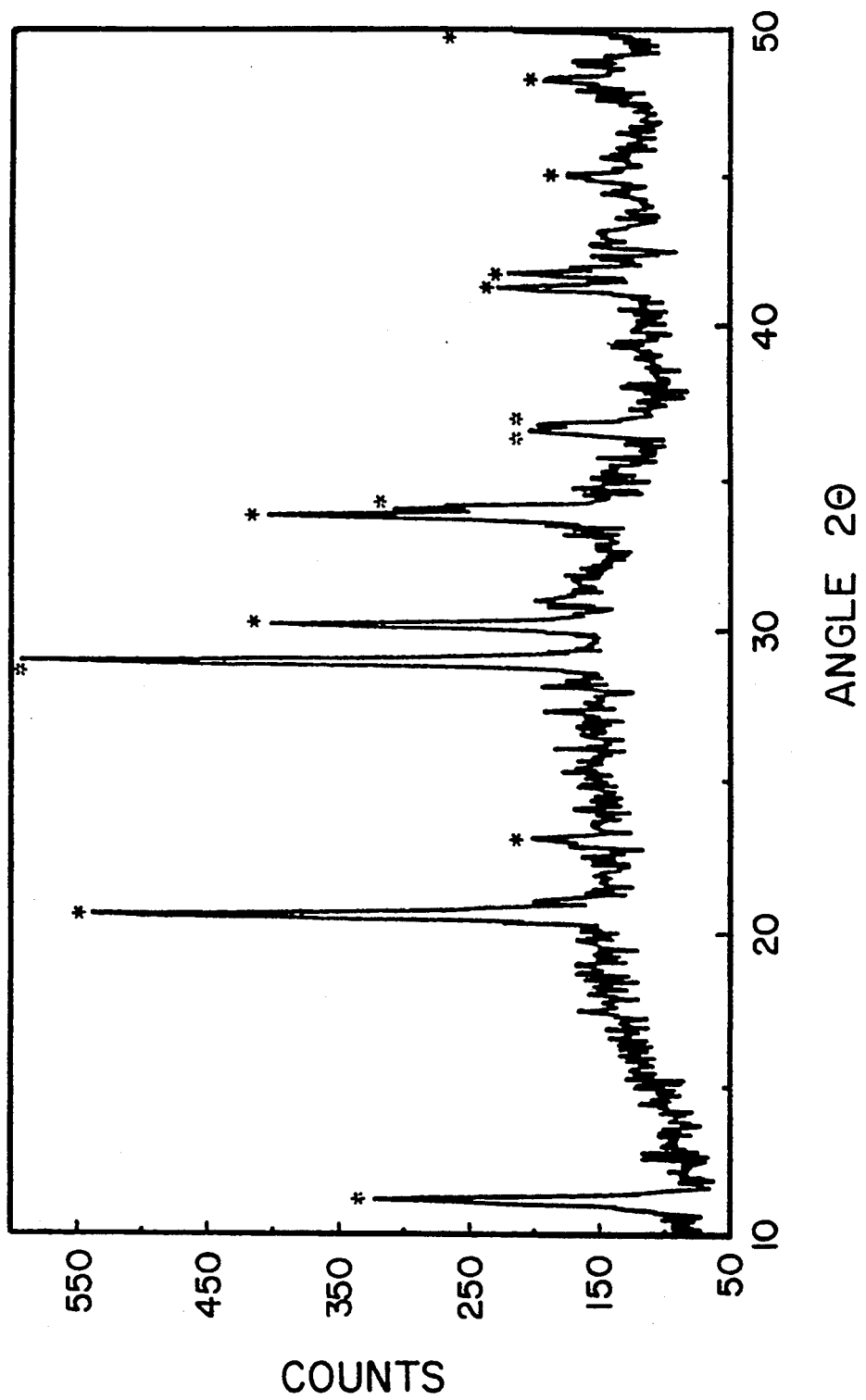
FIG. 2 is an X-ray powder pattern of brushite scraped from the surface of an electrode coated according to this invention.

Deposits shown in FIGS. 1A and 1B are crystalline $CaHPO_4.2H_2O$ (brushite). An X-ray powder pattern of material produced at 10 $mA/cm^2$ is shown in FIG. 2. Reflections that are marked by asterisks (*) in FIG. 2 denote those reflections which are expected based upon d spacings known for brushite. No reflections for brushite expected to be greater than the background level are missing from this pattern. Additionally, there are no reflections present which might be associated with other materials. Determination of the amount of calcium in this material by atomic absorption spectroscopy indicates 22% calcium by weight, which is in good agreement with the value of 23.3% predicted for brushite.

Current efficiencies for production of the brushite coatings on 316L stainless steel are 50% at 10 $mA/cm^2$, 40% at 1 $mA/cm^2$, but only 10% at 0.1 $mA/cm^2$, because the pH perturbation near the electrode surface is not large enough to produce extensive localized crystallization. The current efficiencies were determined gravimetrically using the assumption that 100% current efficiency corresponds to 1 mole of $CaHPO_4.2H_2O$ being deposited per mole of $e^-$ passed. All current efficiencies were calculated for electrodes on which 5 $C/cm^2$ coatings had been deposited.

Figure 3A:
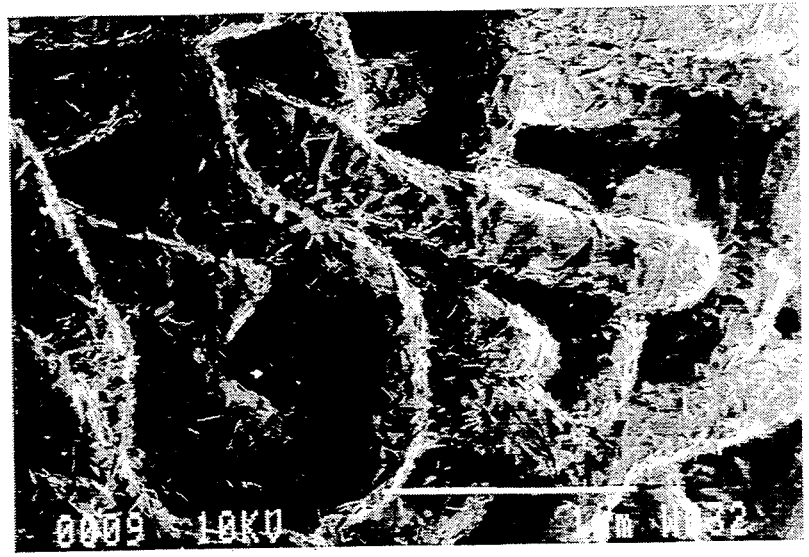
FIGS. 3A and 3B are scanning electron micrographs of electrolytically deposited brushite coatings on titanium mesh.
Figure 3B:
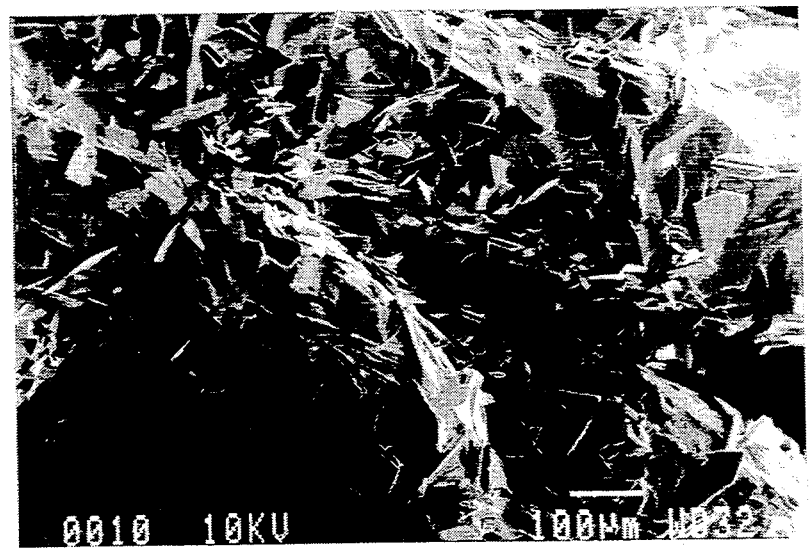

The general applicability of electrolytically deposited phosphate coatings on metal substrates is further exemplified in FIG. 3, wherein scanning electron micrographs of the same coating (at two different magnifications) are as shown. The substrate in this case is titanium mesh on the stem of a commercially available Ti-6Al-4V hip implant. This mesh provides an anchor for bony ingrowth into the implant. Strands of the mesh are the large cylindrical features in FIG. 3, which are 250 $\mu m$ in diameter. Crystallization was carried out at 1.0 $mA/cm^2$ until 8 $C/cm^2$ of charge had passed. The area used to determine the current density was based on the overall dimensions of the electrode, not the actual surface area of the mesh, which was not measured. All of the surfaces visible in FIG. 3 are coated and there are no discernable locations where preferential crystallization appears to have occurred. The morphology and physical integrity of calcium phosphate coatings produced by electrolytic deposition of the instant invention also may be varied using controlled potential electrolysis in order to produce the crystallization.

The results reported in this disclosure are considered to be nominal and continued use of the invention process will yield successful results as herein indicated. Variation in concentrations of electrolytes, electric current densities used and/or the totals of coulombic charges passed may be had without departing from the intent and the spirit of this teaching. Such variations should be considered and readily employed, consistent with the hereinafter appended claims.

What is claimed is:

1. An electrolytically-induced crystallization method for coating a conductive substrate with a biologically compatible, bone-emulating salt comprising:

(a) providing an electrolysis apparatus with a cathode made of a conductive substrate of a conductor which is to be coated with said salt by an electrocrystallization growth process;

(b) preparing for said apparatus an electrolyte characterized as an aqueous solution containing cations and anions derived from the salt to be crystallized onto the cathode, said preparing including initiating a temperature and a pH of the electrolyte that define peak saturation conditions so that when the pH is caused to increase said solution saturates and desired forms of the salt crystallize locally from out said solution and grow on said cathode;

(c) contacting said cathode with said solution; and (d) passing an electric current through said apparatus and controlling the number of crystal nucleation sites and the rate of crystal growth on the cathode by varying said electric current.

2. An electrolysis method for electrolytically coating a conductive substrate with strongly adherent salt crystals obtained from ions of salts that are contained in an aqueous electrolyte, said method comprising using the substrate as a cathode in an electrolysis apparatus, initiating a nominal pH of the electrolyte and electrolyzing the cathode so that hydrogen evolves causing local pH proximate surfaces of the cathode to vary from the nominal causing less soluble forms of said salts in the electrolyte to crystallize out of the electrolyte and adhere in crystalline form to the cathode.

3. The method of claim 2 wherein the ions contained in the aqueous electrolyte are calcium ions and dihydrogen phosphate ions and the nominal pH is 3.5.

4. An irregularly surfaced prosthetic appliance made by the process of claim 1 and comprising a foraminous substrate that is uniformly phosphate crystal-coated and in which a coating is a strongly adherent crystal growth comprising pure brushite, crystals of said growth effective to emulate bone and enhance bone fixation thereto.

5. The appliance of claim 4 wherein said substrate is a metallic mesh.

* * * * *